United States Patent [19]

Carr

[11] Patent Number: 4,647,281
[45] Date of Patent: Mar. 3, 1987

[54] INFILTRATION DETECTION APPARATUS

[75] Inventor: Kenneth L. Carr, Harvard, Mass.

[73] Assignee: M/A-Com, Inc., Burlington, Mass.

[21] Appl. No.: 703,326

[22] Filed: Feb. 20, 1985

[51] Int. Cl.[4] ............................................. A61B 5/00
[52] U.S. Cl. ...................................... 604/50; 604/66;
128/736; 343/718
[58] Field of Search .................. 604/31, 50, 65, 66,
604/67, 245; 128/736, 653, 742; 343/718

[56] References Cited

U.S. PATENT DOCUMENTS

| 4,138,998 | 2/1979 | Nowogrodzki | 128/653 |
|---|---|---|---|
| 4,245,507 | 1/1981 | Samulski | 128/736 |
| 4,275,741 | 6/1981 | Edrich | 128/736 |
| 4,312,364 | 1/1982 | Convert et al. | 128/736 |
| 4,346,716 | 8/1982 | Carr | 128/736 |
| 4,379,461 | 4/1983 | Nilsson et al. | 128/736 |
| 4,416,552 | 11/1983 | Hessemer, Jr. et al. | 128/736 |
| 4,479,498 | 10/1984 | Toftness | 128/736 |
| 4,542,748 | 9/1985 | Roy | 128/736 |

FOREIGN PATENT DOCUMENTS 2000335 1/1979 United Kingdom ............... 128/736

OTHER PUBLICATIONS

Barrett & Myers, "Subcutaneous Temperature: A Method of Noninvasive Sensing", *Science*, Nov. 14, 1975, vol. 190, pp. 669–671.
Dicke, "The Measurement of Thermal Radiation at Microwave Frequencies", *The Review of Scientific Instruments*, Jul. 1946, vol. 17, No. 7, pp. 268–275.
"Passive Subcutaneous Temperature Measurement for Investigation of Thermoregulation", Proceedings of the 8th European Microwave Conference, Paris, France (Sep. 4, 1978).
"Telethermometer", *Polish Technical Review* (Poland) vol. 135, No. 1 (1981).
A Microwave Compatible MIC Temperature Electrode for Use in Biological Dielectrics", Larsen et al, *IEEE Transactions on Microwave Theory and Techniques*, vol. MTT-27, No. 7, Jul. 1979.
Carr, "Compact Dual-Mode Microwave Antenna,'- '*NASA Tech. Briefs*, Spring 1981.

Primary Examiner—C. Fred Rosenbaum
Assistant Examiner—John D. Ferros
Attorney, Agent, or Firm—Wolf, Greenfield & Sacks

[57] ABSTRACT

An apparatus used in association with a needle for infusing a liquid. This apparatus is for detecting the infiltration of the liquid through the vascular wall into the perivascular tissues. The apparatus includes a non-invasive conformal microwave antenna means adapted to be positioned over the area where liquid infusion occurs. A microwave radiometer connects from the antenna means for detecting sub-cutaneous temperature at the site thereof. A reference antenna means is also employed so that a proper temperature differential can be established. In an alternate version of the invention, switching means is provided so that upon detecting an alarm condition, the liquid can be immediately terminated and a neutralizing agent can be introduced to the needle.

23 Claims, 11 Drawing Figures

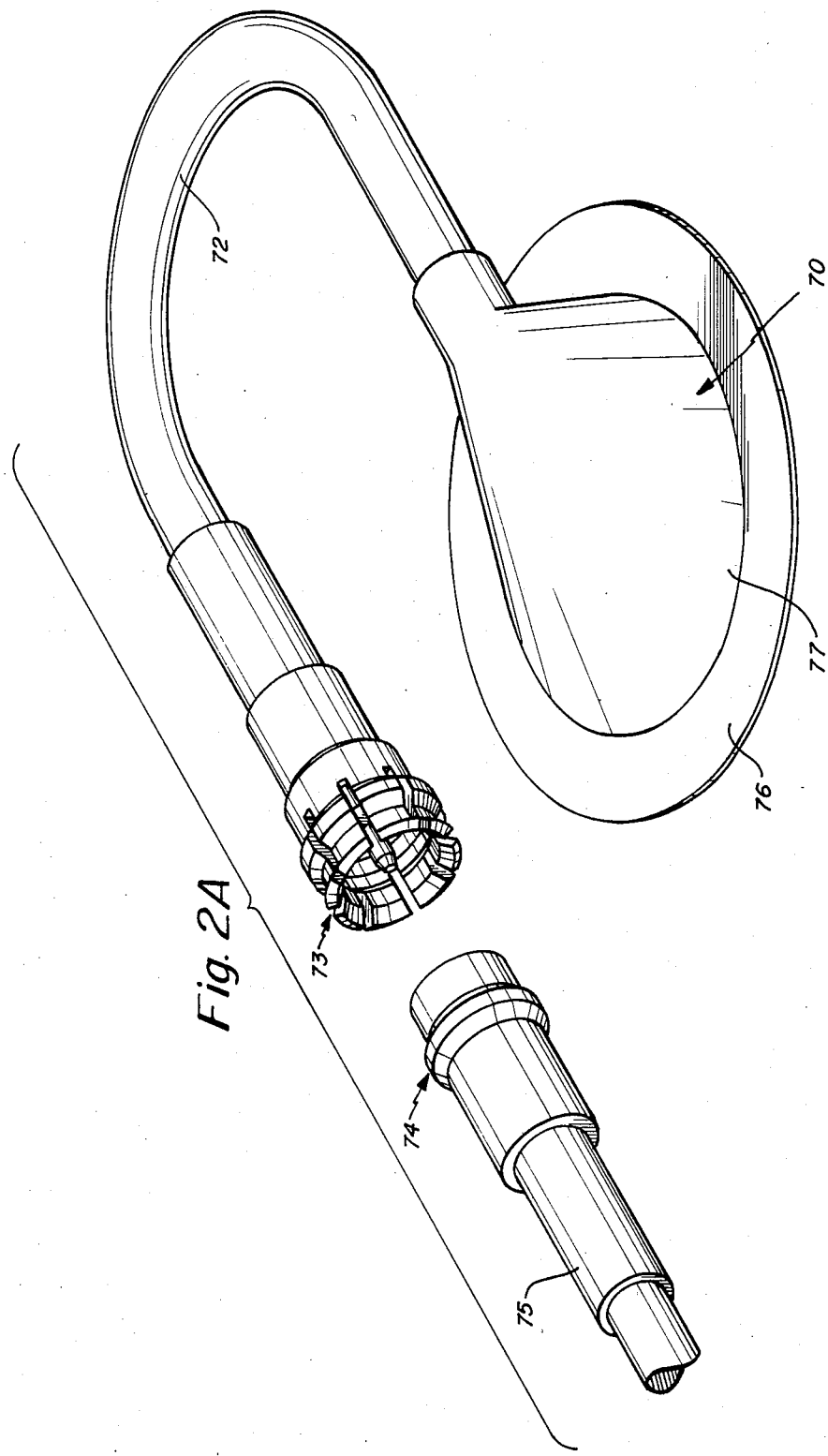

EXTRAVASATION DETECTION

ADRIAMYCIN EXTRAVASATION
RIGHT FORELEG- 6ML USING SYRINGE

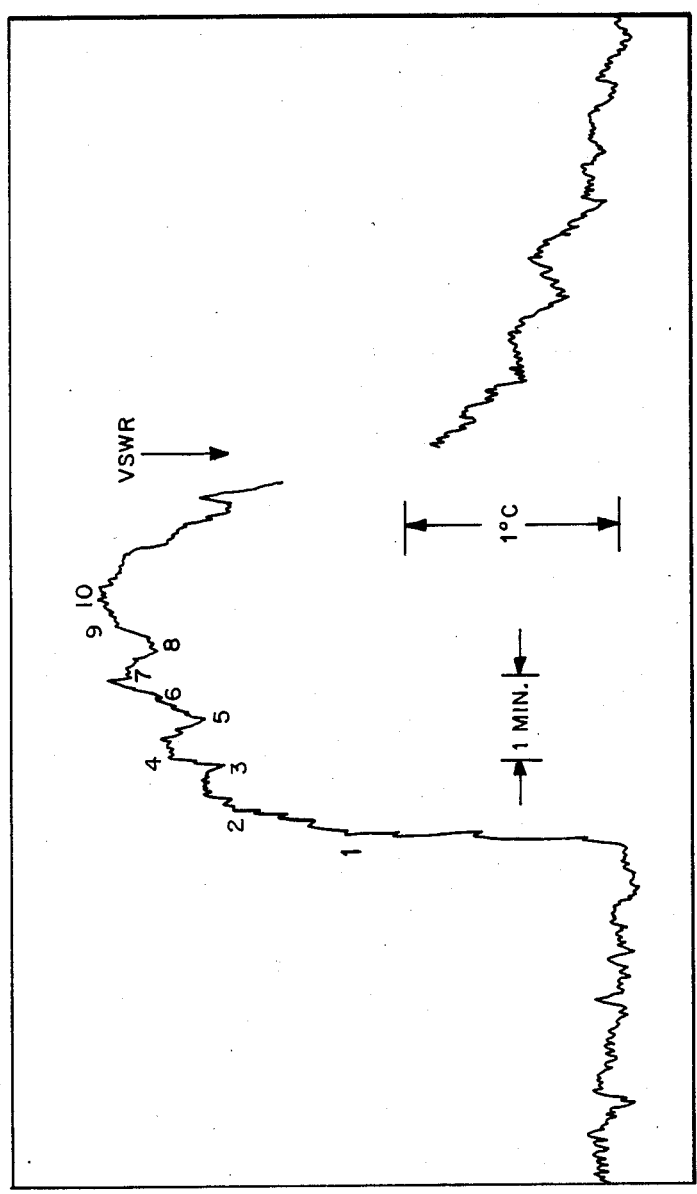

INFILTRATION DETECTION APPARATUS

BACKGROUND OF THE INVENTION

The present invention relates in general to infiltration or extravasation detection apparatus and pertains, more particularly, to infiltration or extravasation detection employing microwave radiometer measurement detection. Using microwave radiometric detection, it is possible to measure sub-surface tissue temperatures and thus provide a more instantaneous response time.

Various liquids such as water, electrolytes, sugar, blood, and pharmaceuticals are commonly administered to hospitalized patients from a container using a needle, commonly referred to as an intravenous needle that is adapted to be inserted into a superficial vein or artery. Any movement by the patient or improper insertion of the intravenous needle causes the tip of the needle to pierce the vascular wall and this causes the liquid that is being administered to undesirably enter the perivascular tissues. When this happens, the liquid may cause discoloration, discomfort and possible destruction of the tissue.

Two prior art patents that show typical infiltration detection systems are U.S. Pat. Nos. 3,618,602 and 4,010,749 both to Robert F. Shaw. Such systems enable detection of liquid infiltration so that the infusion of the liquid can be terminated. However, in connection with the injection of certain toxic liquids, typically used in cancer treatment applications, it is necessary to have extremely early detection of infiltration or extravasation. With thermistor sensor type systems as disclosed in the aforementioned Shaw patents, the response time is simply too slow and is furthermore subject to false alarms due to the need for pressure contact with the surface of the skin. Accordingly, particularly for infusion of more toxic liquids, present techniques are inadequate and can cause serious damage to the patient if the infiltration of the toxic liquid is not detected very early.

Another technique that has been used previously includes a pressure detection technique. More particularly, this technique has attempted to measure the swelling (the pressure build-up) caused by the leaking fluid under the skin. However, this technique also turns out to be ineffective for at least two reasons. The swelling under the skin tended to be broader than a small bubble area. Secondly, there was a significant delay in detection with this technique and thus the response time was extremely poor.

Accordingly, it is an object of the present invention to provide an improved infiltration detection system or apparatus in which the response time of detection is substantially improved in comparison with existing systems.

Another object of the present invention is to provide an improved infiltration detection system employing microwave radiometric detection that provides sub-surface temperature readings that thus provide more accurate detection.

A further object of the present invention is to provide an improved infiltration detection system employing passive, non-invasive apparatus for sub-surface thermal sensing.

SUMMARY OF THE INVENTION

To accomplish the foregoing and other objects, features and advantages of the invention, there is provided an apparatus used in association with liquid-infusion means which apparatus is for detecting the infiltration of the liquid through the vascular wall into the perivascular tissues. The apparatus comprises a non-invasive conformal microwave antenna means that is adapted to be positioned over the area where the liquid infusion occurs. A microwave radiometer is connected from the antenna means for detecting sub-cutaneous temperature at the site thereof. Means are provided for signaling an alarm condition upon detecting of a predetermined temperature. In a preferred embodiment of the present invention described herein, there are actually two antenna means, one which is considered as a primary antenna means position over the area which liquid infusion occurs and a second which is a reference antenna means. With the use of two conformal antennas, then the radiometer outputs respectively therefrom couple to a comparator for providing a temperature differential indication which can trigger an alarm. Moreover, in accordance with another embodiment of the invention described herein, upon reaching an alarm condition, switching means is provided so as to interrupt any further primary liquid flow. This switching means at the same time provides for the coupling of a neutralizing agent to the needle so as to reduce the likelihood of any damage to the patient, particularly if the liquid that is being infused has toxic levels.

BRIEF DESCRIPTION OF THE DRAWINGS

Numerous other objects, features and advantages of the invention should now become apparent upon a reading of the following detailed description taken in conjunction with the accompanying drawing, in which:

FIG. 2A is a perspective view showing an alternate antenna element employing a circular antenna and showing further detail of the associated connector;

FIG. 10 is still a further plot illustrating response time with the system of the present invention.

DETAILED DESCRIPTION

Figure 1:
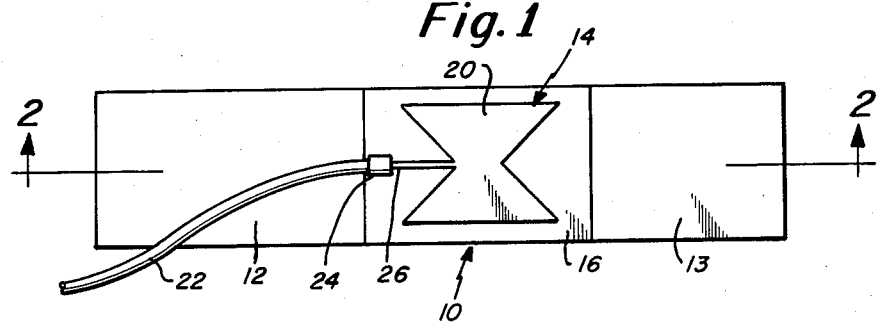
FIG. 1 is a plan view of a first embodiment of the present invention employing a "bow-tie" antenna configuration.
Figure 2:
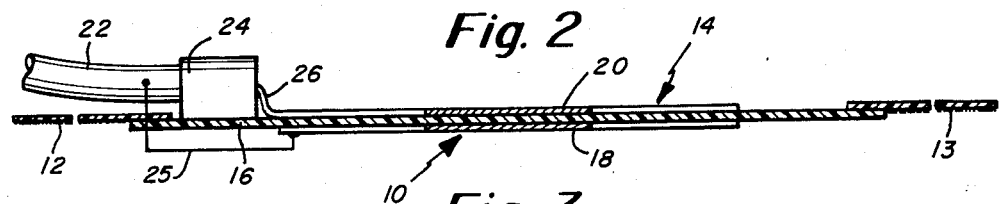
FIG. 2 is a side cross-sectional view taken along line 2—2 of FIG. 1.
Figure 3:
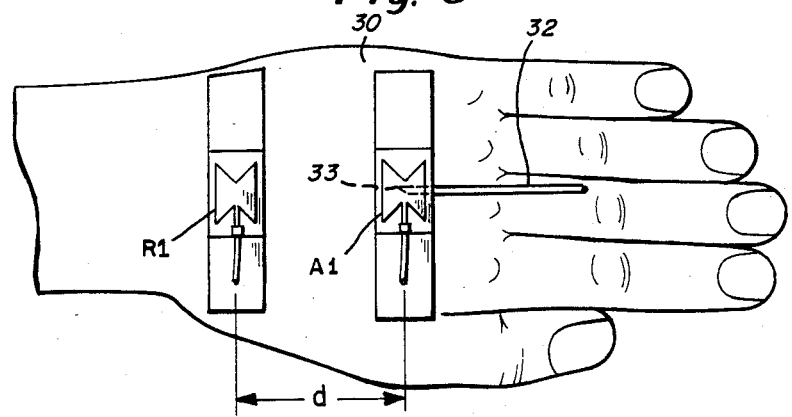
FIG. 3 is a diagram illustrating the placement of a pair of radiometric detectors as in accordance with the invention.
Figure 4:
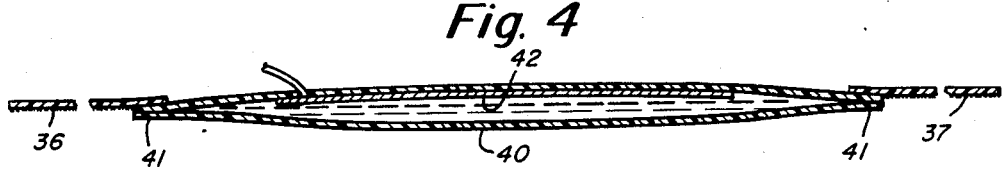
FIG. 4 is a cross-sectional view of an alternate embodiment of the antenna employing a liquid sac.
Figure 5:
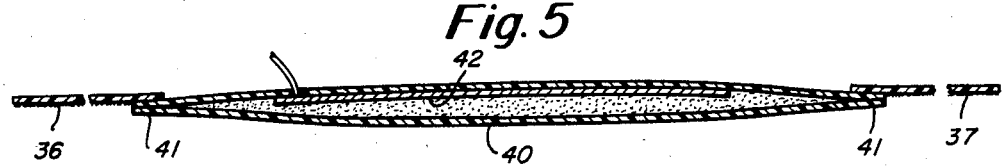
FIG. 5 is still another embodiment of the antenna construction that is used with the invention incorporating a conformal microwave powder sac.

In accordance with the present invention, there is now described herein in further detail, a number of different embodiments of the present invention. For example, a first embodiment of the microwave detector is illustrated in FIGS. 1 and 2 while second and third embodiments thereof are illustrated in FIGS. 4 and 5, respectively. FIG. 3 illustrates the placement of a pair of microwave detectors, one of which is the primary detector adjacent the intravenous needle and the second being a reference detector spaced from the primary detector. FIG. 2A is a perspective view showing an alternate antenna element employing a circular antenna and showing further detail of the associated connector. Also illustrated herein are a series of plots which illustrate the substantially improved response time with the techniques of the present invention. In this regard, with the microwave detection scheme that is employed herein, there is provided a non-invasive technique that is not sensitive to contact pressure as with prior thermistor techniques. Furthermore, the microwave technique that is employed herein measures sub-cutaneous temperatures. This is important from the standpoint that when infiltration or extravasation occurs, it occurs in the perivascular tissues and thus improved response time is realized by virtue of using microwave detection techniques specifically designed for sub-cutaneous readings.

Reference is now made to FIGS. 1 and 2 which together illustrate a first embodiment of the present invention in the form of a conformal antenna element 10 which is comprised of opposite side disposed adhesive strips 12 and 13 and a center antenna section 14. The central section 14 of the antenna element is comprised of a thin flexible plastic layer 16 to which the adhesive strips 12 and 13 are attached. The thin flexible plastic layer 16 has deposited on either side thereof, copper clad layers, including layer 18 and antenna layer 20 which is also of copper. The top plan view of FIG. 1 shows the configuration of the antenna element 20. This is a "bow-tie" arrangement. However, many other configurations of antenna may be employed. FIG. 1 illustrates the antenna 20 being coupled to a coax line 22 by way of a connector 24 and a thin conductive strip 26 (strip 26 represents the continuation of the coax center conductor).

Reference is now also made to FIG. 2A that shows an alternate version of the antenna element. In this case the antenna is in the form of a circular patch antenna 70 shown connecting to the coax cable 72 and from there to a connector which is comprised of connector parts 73 and 74. The other cable segment 75 illustrated in FIG. 2A couples to the radiometer such as illustrated in the block diagram of FIG. 6. In FIG. 2A the patch antenna 70 may be constructed similarly to the embodiment of FIGS. 1 and 2 including a substrate 76 having a conductive circular antenna 77 deposited thereon. FIG. 2A illustrates the coaxial cable 72 coupling to the patch antenna 70. The outer conductor of the coax cable may simply be terminated while the inner conductor connects directly to the circular antenna element 77. In addition to the "bow-tie" antenna illustrated in FIGS. 1 and 2 and the circular or ring antenna illustrated in FIG. 2A, there are other forms of patch antennas that may be employed, such as one of rectangular or square patch shape. In each instance, the microwave signal is picked up at the antenna and this signal is coupled by way of the coaxial cable and connector to the radiometer.

It has been mentioned previously that the outer conductor of the coax such as in FIGS. 2 or 2A may terminate or simply float. However, in a preferred embodiment of the invention, the outer conductor, as illustrated in FIG. 2 connects as illustrated by the lead 25 in FIG. 2 to the conductive layer 18. In an alternate version of the invention, the layer 18 may be a mesh screen which enables one to see therethrough to the antenna element 20. The viewability of the antenna element is preferred so that it can be properly oriented, with the antenna element being in contact with the skin.

It is further noted in FIG. 2 that the adhesive strips 12 and 13 are attached to the top side of the layer 16. They could just as easily be attached to the bottom side of the layer. In either instance, the adhesive surface is the top surface as viewed in FIG. 2 assuming that the antenna element 20 is placed against the skin. With regard to the embodiment of FIG. 2, should the connector 24 be in the way as far as proper connection is concerned, then the connector 24 can be placed on the opposite side of the substrate 16. Again, because microwave detection is being employed, the intimacy of contact between the antenna element and the skin is not as critical as when using a thermistor which relies upon direct intimate contact with the skin.

In either case of having the outer conductor floating or attached to a conductive plate, it is noted that, for example, in FIG. 2, the center conductor 26 may be secured to the antenna element by solder or by some type of a compression fit therewith.

FIG. 3 illustrates the manner of placement of the conformal antenna elements illustrated in FIGS. 1 and 2. In FIG. 3 these elements are identified as elements A1 and a separate spacedly disposed element R1. FIG. 3 illustrates the placement of these antenna elements relative to a subject's hand 30. Of course, in accordance with the invention, the antenna elements may be used on any part of the body of where an intravenous injection is being made.

In FIG. 3 there is shown the end of a needle 32 which is adapted to infuse a liquid into the body. Hereinafter, examples are given of types of liquids that are infused and experiments that have been carried out along with associated plots that have been taken particularly of response time. It is also noted in FIG. 3 that the comformal antenna element A1 is adapted to be disposed at a point over the position where the needle is piercing into the skin. The pierced portion of the needle is illustrated in FIG. 3 at 33 by dashed line.

As previously indicated, it is desired that the conformal antenna element 10 such as illustrated in FIGS. 1 and 2 be flexible and readily conform to the shape of the skin. Moreover, it is preferred that the conformal antenna element be constructed relatively inexpensively so that it can be of disposable type. Even though the conformal antenna element is made flexible and is to conform to the shape of the skin, it provides proper temperature detection even if there is some variation in spacing between the antenna element and the skin. As indicated previously in the prior art thermistor arrangement, proper direct and intimate contact had to be provided in order to obtain a proper thermal reading.

In FIG. 3 the antenna elements A1 and R1 are shown spaced a distance d. It is preferred that this spacing be as close as possible for convenience and to also establish a substantially zero temperature differential absent detection. However, the spacing cannot be too close as this could effect proper detection, particularly if there is infiltration under the detector R1. The antenna elements are preferably sufficiently spaced so as to provide the proper temperature differential caused by the infiltration. A preferred spacing for the elements is on the order of one-half wavelength at the operating frequency.

FIG. 4 shows an alternate embodiment of the conformal antenna element, also including oppositely disposed adhesive strips 36 and 37 in a central antenna section which is comprised of a plastic bag 40. The plastic bag 40 may be formed from two separate plastic pieces that are joined at the opposite ends 41. In antenna element 42 is printed on the inner surface of the bag 40 as indicated. This antenna element 42 may take on many different configurations such as even the configuration of the element 20 in FIG. 1. In order to provide a more conformal arrangement, the plastic bag 40 is filled with a de-ionized water and thus there is very good conformal matching of the antenna element to the skin. There is also a good match microwave-wise between the plastic bag containing water and the surface of the tissue.

The embodiment of FIG. 5 is quite similar to that described in FIG. 4 and thus similar reference characters are employed. In FIG. 5 there are shown the adhesive end strips 36 and 37 which are used for attachment of the conformal antenna element to the surface of the skin. There is also provided a plastic bag having the antenna element 42 printed therein. In the embodiment of FIG. 5 rather than employing a de-ionized water fill, the plastic bag 40 is filled with a microwave powder. Such an arrangement also provides microwave matching to the surface of the tissue and also provides a structure that is flexible or conformal to the tissue surfaces.

In either the embodiment of FIG. 4 or FIG. 5 with the use of the plastic sack or pillow, this can be filled with either powder or a liquid as long as it provides the ability to conform (i.e. be flexible) to the skin or tissue. The dielectric material in the pillow or sack should also have matching dielectric properties properly couple the signal from the tissue to the antenna.

In a preferred version of the present invention, the embodiments illustrated in FIGS. 1-5 are preferably disposable. However, if ongoing medical costs are of concern, then the antenna need not be a throw away item. In this case, one would then construct a more expensive reusable antenna.

Figure 6:
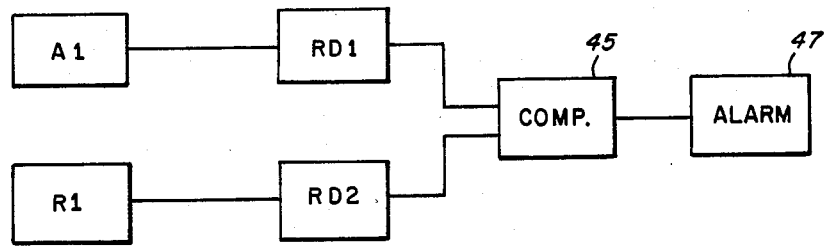
FIG. 6 is a block diagram associated with the apparatus of the present invention.

FIG. 6 is a block diagram illustrating the overall system of the present invention. FIG. 6 shows the conformal antenna elements A1 and R1. The output of the antenna element A1 couples to the radiometer RD1. Similarly, the output of the reference antenna element R1 couples to the radiometer RD2. Both of the radiometers RD1 and RD2 may be of the type illustrated in U.S. Pat. No. 4,346 716. The radiometer RD1 has an output voltage that is proportional to the temperature measured from the antenna element A1. Similarly, the output from the radiometer RD2 is a voltage level corresponding to the temperature measured at the reference antenna element R1.

The two outputs from the radiometers RD1 and RD2 couple to a comparator 45. This comparator compares the voltages and thus the temperatures detected and when a sufficient temperature differential is detected between the elements A1 and R1, then there is an output at the comparator which couples to the alarm 47.

In the block diagram of FIG. 6, reference is made to the use of two radiometers RD1 and RD2. However, it may be preferred to use a single radiometer. Thus, it is preferred to use a single radiometer which is time shared between the two antennas. In this connection, a Dicke radiometer may be employed such as of the type described in U.S. Pat. No. 4,346,716. In this connection and with regard to the circuit described in this patent, it is noted that the reference load described therein corresponds to the reference antenna referred to herein.

For the most part, the antenna element 41 senses body temperature and thus assuming that the liquid is being properly intravenously fed, the antenna element A1 also for the most part detects body temperature. There is thus no temperature differential and thus no alarm indication is given. On the other hand, should the liquid that is being infused via the needle 32 pierce the vascular wall and cause the liquid being administered to flow in the perivascular tissues, then there is an immediate detection of the liquid temperature. Because this liquid temperature is typically at room temperature or many times at an even lower temperature, because it is kept refrigerated, there is a temperature differential that is then detected. Furthermore, because of the use of microwave radiometric detection techniques, this detection occurs with a very rapid response time as illustrated herein.

Figure 8:
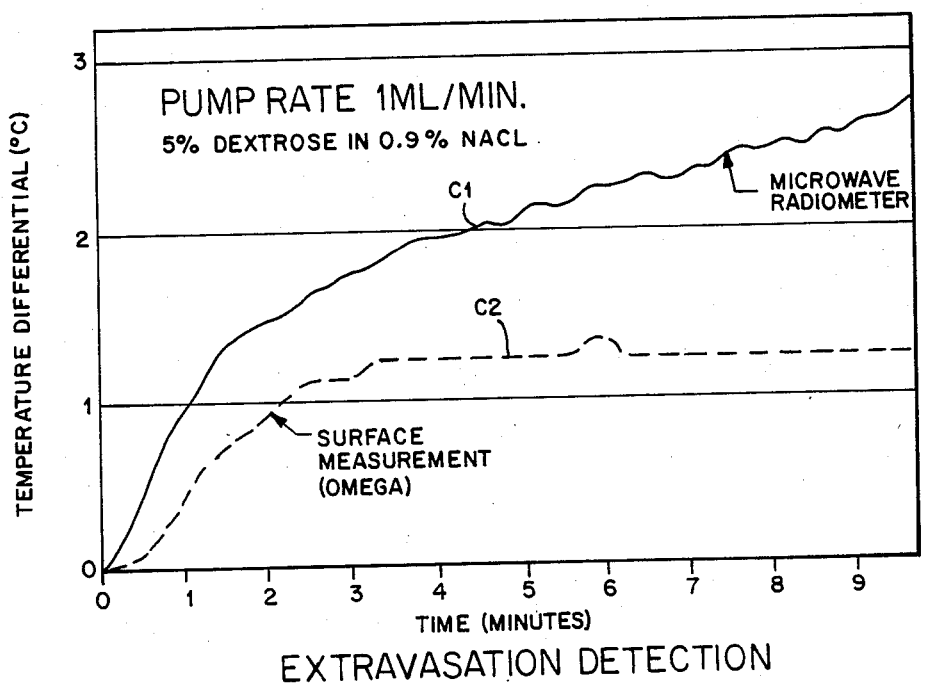
FIG. 8 is a comparison plot showing response time of a system of the present invention in comparison with a prior art thermistor sensor.

Reference is now made to FIG. 8 which shows a very clear comparison of response time between the technique of the present invention and a thermistor sensing arrangement. In FIG. 8 the curve C1 illustrates the response time for the technique of the present invention and the curve C2 represents the response time with a thermistor sensor such as of the type illustrated in the aforementioned Shaw patents. In FIG. 8 both of the plots show on the X axis time increments and on the Y axis temperature differential. It can be seen readily that particularly at the first time unit, the temperature differential for curve C2 is about one-half of the temperature differential for the curve C1. This indicates at least a two to one ratio in initial response between the two different techniques.

In the two plots of FIG. 8, the measurements have been taken with a liquid solution of 5% dextrose and 0.9% NaCl. The liquid was infused at a pumping rate of one milliliter per minute. Assuming that the pumping rate is constant, thus the X-axis and FIG. 8 may be a measure of time units for volume infused.

Figure 9:
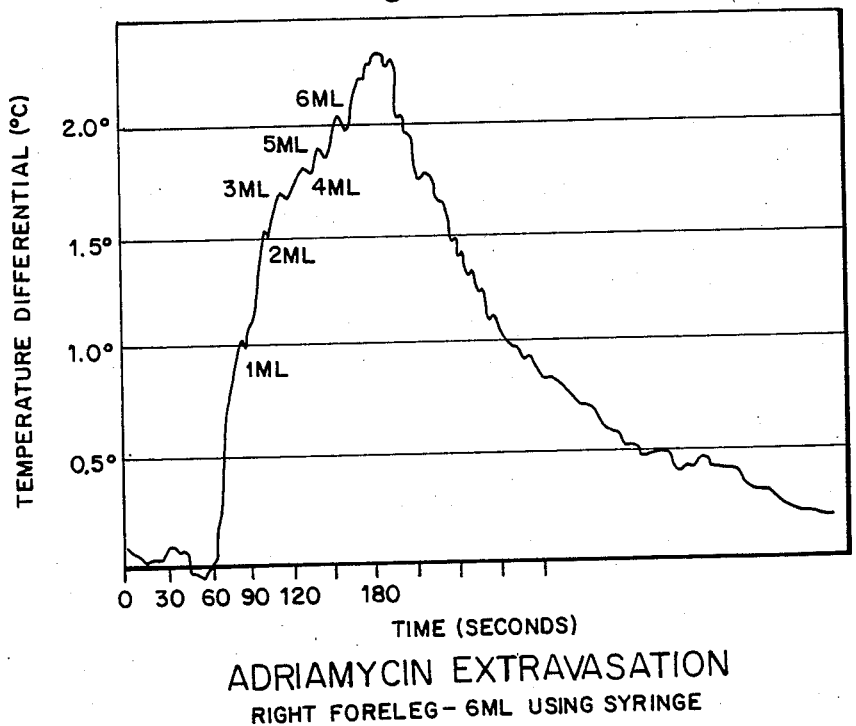
FIG. 9 is another plot of response time.

FIG. 9 illustrates another plot showing the radiometer response associated with an extravasation produced on the right foreleg of a dog using a syringe to inject 6 milliliters of adriamycin (2 mg/ml). In FIG. 9 the X-axis represents time and the Y-axis represents temperature differential. On the curve that is illustrated, there are also found a series of numbers from 1 through 6. These represent the successive injection of the 6 milliliters of liquid one milliliter at a time. In FIG. 9 the time from 0 to 60 seconds that is illustrated establishes the base line at L1 for measurement of the temperature differential. During the time period from 60 to 90 seconds, one milliliter of solution has been injected causing a temperature change of approximately 1° C. This is indicated at the commencement of the response curve at L2 in FIG. 9. This curve clearly illustrates the instantaneous response that is possible with the system of the invention. As the temperature begins to stabilize and turn slightly toward the base line, a second milliliter of solution is injected causing a further increase in temperature as noted to approximately 1.5° C. temperature differential. Gradually, the complete six milliliters of solution is injected, resulting in a total temperature change of approximately 2.3° C. Thereafter, the radiometer is momentarily disconnected from the antenna to allow for a measurement of antenna match (VSWR). Eventually, as noted in FIG. 9, the temperature returns to the normal base line temperature.

In connection with FIG. 9 it has been noted that reference has been made to the temperature differential 1° C. This may be established as a temperature differential threshhold level. However, when infusing toxic liquids, it is preferred to have a lower threshhold in order to turn the pump off as quickly as possible in the event of pumping of liquid into the patient. In such as case, then it is preferred to have detection occur at a temperature differential on the order of ½° C.

FIG. 10 shows another illustration of the response of the system of the invention. This one being associated with an extravasation of 10 milliliters of adriamycin in the right hind outer leg of a dog. Again, there is noted in this plot also, an extremely fast response time in which there is an immediately temperature differential of at least 1° C. caused by injection of a single milliliter of the 10 milliliters of the solution.

Figure 7:
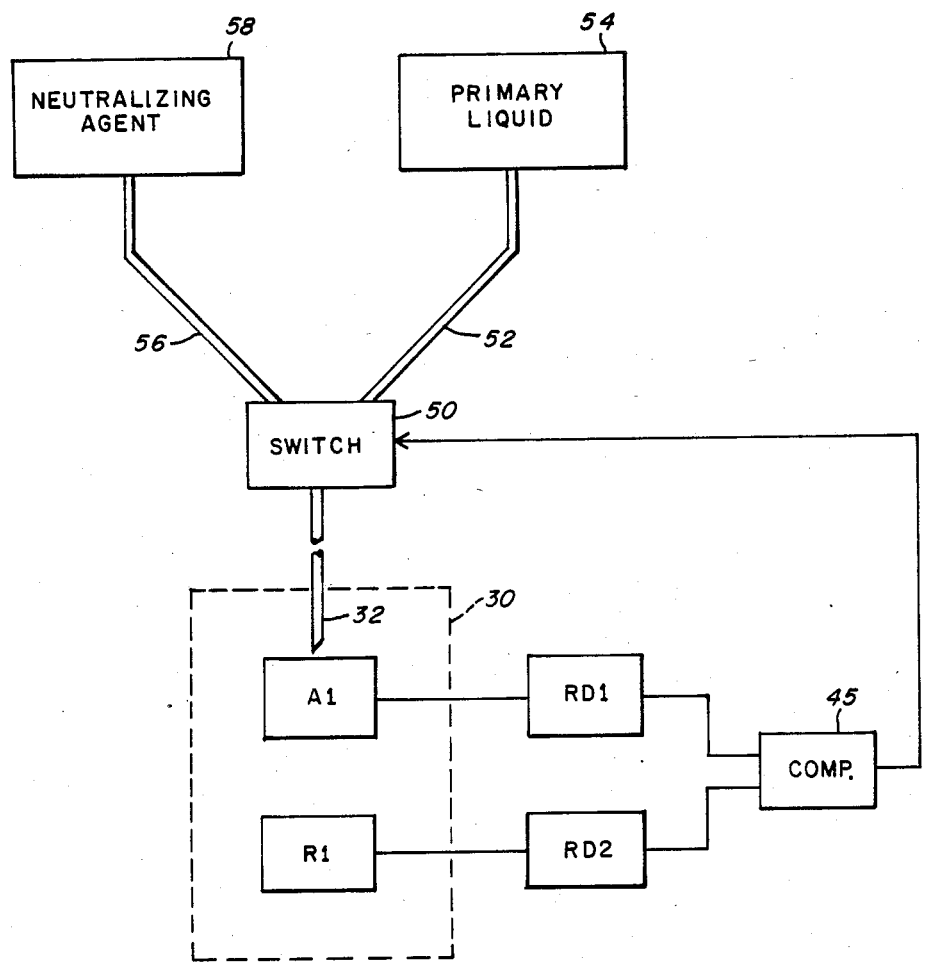
FIG. 7 is a block diagram of an alternate version of the present invention including the switching means for introducing a neutralizing agent to the needle upon detection of infiltration.

FIG. 7 illustrates a further feature of the present invention. In FIG. 7 there is shown a block diagram which illustrates some of the components previously described in connection with the block diagram of FIG. 6. Thus, there is shown the conformal antenna elements A1, and R1; element R1 being the reference element. These antenna elements coupled to the respective radiometers RD1 and RD2. The two output signals from the radiometers couple to the comparator 45. When there is a sufficient temperature differential detected between the two antenna elements, then there is an output from the comparator 45 which controls the switch 50. Switch 50 is considered to be of conventional design and simply is adapted to be electrically controlled but operated so as to mechanically switch so as to couple either the primary liquid to the needle or the neutralizing agent to the needle. FIG. 7 shows the needle 32 being actually an output from the switch 50. The switch 50 also has input lines coupling thereto including a line 52 coupled from the primary liquid source 54 and a line 56 coupled from the neutralizing agent source 58.

The system illustrated in FIG. 7 is primarily adapted for use when one is injecting toxic solutions in which case it is desired to not only terminate injection of the primary liquid as rapidly as possible, but it is also necessary to introduce a neutralizing agent to the infiltrated area. The neutralizing agent neutralizes the toxicity of the primary liquid so that any severe damage to the patient is prevented.

Under normal operation, when there is no temperature differential, the output of the comparator 45 is at a level in which the switch 50 is controlled so that the primary liquid is coupled by way of the line 52 to the output at the needle 32. The switch 50 is essentially a bi-directional switch which is actuated to a second position when the comparator 45 triggers. The comparator 45 is triggered upon detecting a sufficient temperature differential between the conformal antenna elements A1 and R1. When this occurs, as indicated previously, the switch 50 reverts to its opposite position and there is a mechanical coupling of the neutralizing agent by way of the line 56 to the needle 32. The switch operation is in a mutually exclusive manner so that when the comparator 45 signals the switch to actuate it, the switching function is not only to introduce the neutralizing agent, but is also to terminate the flow of primary liquid. Thus, on receipt of a signal indicating a sufficient temperature differential, this indicates an alarm condition in which basically two actions take place in connection with the arrangement of FIG. 7. The first action is to terminate the primary liquid flow immediately. The second action is to infuse a sufficient neutralizing agent so that damage is prevented. Because of the very rapid response time with the system of the present invention, the primary liquid can be interrupted very quickly and the neutralizing agent can also be applied very quickly so that the chance of any substantial damage to the patient is absolutely minimal.

One embodiment of the invention has previously been illustrated in FIG. 6 which illustrates the use of a separate reference antenna element. In a simplified embodiment of the present invention, only a single conformal antenna element may be employed in which case the output of the radiometer is then simply set up to establish a triggering condition upon reaching some predetermined temperature. Because the liquid that is being infused is usually several degrees colder than body temperature, the output from the radiometer may simply be coupled to a device that will measure the attaining of some predetermined lower temperature than body temperature at which triggering of the alarm occurs. In connection with this alternate embodiment, it is noted that the internal reference load of the radiometer may be employed as the reference.

Having now described a limited number of embodiments of the present invention, it should now be apparent to those skilled in the art that numerous other embodiments and modifications thereof are contemplated as falling within the scope of the present invention as defined by the appended claims.

What is claimed is:

1. A method for rapidly detecting the infiltration of a liquid from a source thereof through the vasuclar wall into the perivascular tissue, comprising the steps of, providing a non-invasive conformal microwave antenna, disposing said antenna on the skin at the area where liquid infusion into a blood vessel is to occur, establishing a reference, providing a microwave radiometer coupled from said microwave antenna, detecting the sub-cutaneous temperature at the site of the antenna with the use of said microwave radiometer, and rapidly signaling as alarm condition upon detecting a predetermined temperature differential between temperature sensed by said microwave radiometer and said reference.

2. A method as set forth in claim 1 further including providing a second non-invasive conformal microwave antenna used as a reference antenna to establish said reference and spacedly disposing said second antenna from said first antenna that is positioned over the area where liquid infusion occurs.

3. A method as set forth in claim 2 including providing a second microwave radiometer connected from the second antenna for also detecting sub-cutaneous temperature at the site of the second antenna.

4. A method as set forth in claim 3 comprising providing a comparator coupled from the outputs of the respective microwave radiometers, said comparator providing an output trigger signal when the temperature differential reaches a predetermined value.

5. A method as set forth in claim 4 including providing a source of neutralizing agent and switching between said source of neutralizing agent and said liquid source so that in one instance there is a coupling of said liquid to the liquid infusion means and having another state responsive to the triggering of said comparator means for interrupting primary liquid flow to the liquid infusion means and instead coupling the neutralizing agent to the luquid-infusing means.

6. A method as set forth in claim 1 wherein said apparatus has a fast response time providing at least 1° C. of temperature differential for one milliliter of infusion.

7. A method as set forth in claim 1 including providing on said non-invasive conformal microwave antenna oppositely disposed adhesive strips and a central antenna section.

8. A method as set forth in claim 7 wherein said central antenna section comprises a flexible plastic layer having a metallic antenna configuration on at least one side thereof.

9. A method as set forth in claim 8 wherein said antenna configuration is of bow-tie shape.

10. A method as set forth in claim 9 including providing a second conductive layer on the opposite side of said plastic sheet.

11. A method as set forth in claim 7 wherein said central antenna section comprises a plastic bag that is liquid filled.

12. A method as set forth in claim 7 wherein said central antenna section comprises a plastic bag that is powder filled.

13. A method as set forth in claim 7 wherein said central antenna section comprises a plastic bag that is liquid filled and that has an antenna element disposed on the inner surface thereof.

14. A method as set forth in claim 7 wherein said central antenna section comprises a plastic bag that is filled with microwave powder and which has an antenna element disposed on the inside surface thereof.

15. A method of rapidly detecting liquid-infusion infiltration into the skin of a patient from a liquid source of infusion liquid in which there is provided a liquid-infusion delivery conduit placed into a blood vessel of the patient for delivery of the infusion liquid into the blood vessel of the patient, said method comprising the steps of, providing a non-invasive conformal and substantially planar microwave antenna, disposing said antenna on the skin at the area where liquid infusion into the blood vessel is to occur, continuously monitoring sub-cutaneous temperature at the site of the antenna as the liquid is infused with the use of a microwave radiometer, and signaling an alarm condition upon detecting a predetermined temperature deviation from normal skin temperature.

16. A method as set forth in claim 15 including providing a second antenna spaced from the first antenna for establishing a reference temperature so as to determine said predetermined temperature deviation.

17. A method as set forth in claim 16 including spacing said second antenna from said first antenna by a distance on the order of one-half wavelength of the operating frequency of the microwave radiometer.

18. A method as set forth in claim 16 including providing a first radiometer associated with the first antenna and a second radiometer associated with the second antenna.

19. A method as set forth in claim 18 including providing a comparison between the output temperatures sensed by the first and second radiometers to determine temperature deviation.

20. A method as set forth in claim 16 including a single radiometer that is switched to read in sequence both antennas.

21. A method as set forth in claim 15 including providing a source of neutralizing agent and providing a switch to switch between neutralizing agent and liquid-infusion source.

22. A method as set forth in claim 21 wherein the liquid is coupled to the blood vessel until a predetermined temperature deviation is detected in which case the coupling of the neutralizing agent is to the blood vessel.

23. A method as set forth in claim 15 including establishing a reference signal and comparing the temperature sensed by the microwave radiometer with said reference signal.

* * * * *